(12) United States Patent
Hamamatsu et al.

(10) Patent No.: US 7,817,261 B2
(45) Date of Patent: Oct. 19, 2010

(54) METHOD OF APPARATUS FOR DETECTING PARTICLES ON A SPECIMEN

(75) Inventors: Akira Hamamatsu, Yokohama (JP); Minori Noguchi, Hitachinaka (JP); Yoshimasa Ohshima, Yokohama (JP); Sachio Uto, Yokohama (JP); Taketo Ueno, Fujisawa (JP); Hiroyuki Nakano, Yokohama (JP); Takahiro Jingu, Takasaki (JP); Hisashi Hatano, Kamisato (JP); Yukihisa Mohara, Kamisato (JP); Seiji Otani, Kamisato (JP); Takahiro Togashi, Kamisato (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 12/114,139

(22) Filed: May 2, 2008

(65) Prior Publication Data
US 2008/0204724 A1     Aug. 28, 2008

Related U.S. Application Data

(63) Continuation of application No. 11/086,442, filed on Mar. 23, 2005, now Pat. No. 7,369,223.

(30) Foreign Application Priority Data
Mar. 29, 2004     (JP)     ............................. 2004-094146

(51) Int. Cl.
G01N 21/00     (2006.01)
(52) U.S. Cl. ................................. 356/237.2; 356/237.1

(58) Field of Classification Search ... 356/237.1–237.6, 356/238.1–238.3, 239.3, 338, 367–369, 430–431; 250/559.11–559.18, 559.44–559.48, 559.24, 250/548
See application file for complete search history.

(56) References Cited

U.S. PATENT DOCUMENTS

| | | | |
|---|---|---|---|
| 6,310,689 B1 | 10/2001 | Ishikawa et al. | |
| 6,411,377 B1 | 6/2002 | Noguchi | |
| 6,654,111 B2 | 11/2003 | Isozaki et al. | |
| 6,657,714 B2 | 12/2003 | Almogy et al. | |

(Continued)

FOREIGN PATENT DOCUMENTS

JP     62-089336     4/1987

(Continued)

*Primary Examiner*—Gregory J Toatley, Jr.
*Assistant Examiner*—Tri T Ton
(74) *Attorney, Agent, or Firm*—Antonelli, Terry, Stout & Kraus, LLP

(57) ABSTRACT

A method and apparatus of detecting a defect by inspecting a specimen in which a surface of a specimen on which plural patterns are formed is illuminated with an elongated shape light flux from one of plural directions which are different in elevation angle by switching an optical path of the light flux emitted from an illuminating light source in accordance with a kind of defect to be detected. Plural optical images of the specimen illuminated by the elongated shape light flux are captured with plural image sensors installed in different elevation angle directions by changing an enlarging magnification in accordance with a density of the pattern formed on the sample in an area irradiated with the illuminating elongated shape light flux. A defect on the specimen is detected by processing the images captured by the plural image sensors.

14 Claims, 12 Drawing Sheets

U.S. PATENT DOCUMENTS

| | | |
|---|---|---|
| 6,778,267 B2 | 8/2004 | Drake |
| 7,046,353 B2 | 5/2006 | Isozaki et al. |
| 7,369,223 B2 * | 5/2008 | Hamamatsu et al. ..... 356/237.2 |
| 2005/0052644 A1 | 3/2005 | Lewis et al. |

FOREIGN PATENT DOCUMENTS

| | | |
|---|---|---|
| JP | 63-135848 | 6/1988 |
| JP | 01-117024 | 5/1989 |
| JP | 08-271437 | 10/1996 |
| JP | 11-064234 A | 3/1999 |
| JP | 2000-105203 | 4/2000 |
| JP | 2001-060607 | 3/2001 |
| JP | 2004-93252 | 3/2004 |

* cited by examiner

METHOD OF APPARATUS FOR DETECTING PARTICLES ON A SPECIMEN

CROSS REFERENCE TO RELATED APPLICATION

This application is a continuation application of U.S. application Ser. No. 11/086,442, filed Mar. 23, 2005, now U.S. Pat. No. 7,369,223 the contents of which are incorporated herein by reference.

BACKGROUND OF THE INVENTION

The present invention relates to a method and apparatus for detecting a particle present on a thin film board, a semiconductor board or a photomask in the process of fabricating a semiconductor chip or a liquid crystal product. The present invention also relates to a method and apparatus for detecting a defect produced at a circuit pattern and inspecting the situation which may have caused production of a particle or a defect in a step of fabricating a device which is subjected to a measurement by analyzing the detected particle or defect.

In a step of fabricating a semiconductor device, when a particle is present on a semiconductor board (wafer), the particle may constitute the cause of an insulation failure or a shortcircuit of the wiring. Further, in accordance with the demand for miniaturization of a semiconductor element, a fine particle also constitutes a cause of an insulation failure of a capacitor or the destruction of a gate oxide film. The particles are mixed at various stages due to various causes, and they may be produced from a movable portion of a carrying apparatus, produced from the human body, produced by a reactor in a processing apparatus by a process gas, or mixed with a drug or a material.

Similarly, also in a step of fabricating a liquid crystal display element, when a particle is mixed on a pattern or some defect is produced, the display element cannot be used. The situation stays the same also in a step of fabricating a printed board, and a shortcircuit of a pattern or a failure in a connection may be caused by such a particle.

As one of the technique for detecting a particle on a semiconductor board, JP-A-62-89336 (Patent publication 1), discloses a method of effecting a highly sensitive and highly reliable inspection of a product for a particle or other defect by eliminating false information in a pattern by irradiating a laser beam onto a semiconductor board, detecting light scattered from a particle produced when the particle is adhered onto the semiconductor board, and comparing a result of inspecting a semiconductor board of the same kind that was inspected immediately therebefore. Further, JP-A-63-135848 (Patent publication 2) discloses a method which involves irradiating laser light onto a semiconductor board, detecting light scattered from a particle which is adhered on the semiconductor board and analyzing the detected particle by laser photoluminescence or an analyzing technology of secondary X-ray analysis (XMR).

Further, as a technique for inspecting a wafer to detect the presence of a particle, there is a method which involves irradiating coherent light to the wafer, removing light emitted from a repeated pattern on the wafer using a spatial filter and emphasizing the received pattern to detect a particle or a defect which is not provided with repeatability. Further, a particle inspecting apparatus is described in JP-A-1-117024 (Patent publication 3) in which a circuit pattern formed on a wafer is irradiated from a direction which is inclined relative to a main group of linear lines of the circuit pattern by 45 degrees to prevent 0-order diffracted light from the main group of linear lines from being incident on an aperture of an object lens. According to this technique, it is also proposed to block light from other groups of linear lines, which are not the main group of linear lines using a spatial filter.

Further, an apparatus and a method of inspecting an object for a defect in the form of a particle or the like is described in, for example, JP-A-8-271437 and JP-A-2000-105203 (Patent publications 4). Particularly, in JP-A-2000-105203, it is proposed to change the size of a detected pixel by switching the detecting optical system. Further, a technique for measuring the size of a particle is described in, for example, JP-A-2001-60607 (Patent publication 5).

However, according to the techniques proposed in the above-cited publications, consideration is not given to a constitution capable of detecting a fine particle or a defect, on a board on which a repeated pattern are mixed, and a non repeated pattern with high sensitivity and at high speed. That is, according to the technologies disclosed in the above-described publications, consideration is not given to a constitution capable of achieving a detection sensitivity (minimum detected particle dimension) equivalent to that of a repeated pattern even at areas other than the repeated pattern portion of, for example, a memory cell portion.

Further, according to the technologies disclosed in the above-described publications, consideration is not given to a constitution capable of promoting a good sensitivity in detecting a small particle or a defect at the 0.1 μm level in a region having a high pattern density. Further, according to the technologies disclosed in the above-described publications, consideration is not given to a constitution capable of promoting a good sensitivity in detecting a particle or a defect that produces a shortcircuiting of wirings or a good sensitivity in detecting a particle in the shape of a thin film. Further, according to the technology disclosed in JP-A-2001-60607, consideration is not given to a constitution capable of promoting an increased accuracy in the measurement of a particle or a defect.

Further, according to the technology disclosed in JP-A-2001-60607, consideration is not given to a constitution capable of promoting a good sensitivity in detecting a particle on a surface of a wafer formed with a transparent thin film.

SUMMARY OF THE INVENTION

The present invention provides a method of inspecting a defect in the form of a small particle or other defect of the 0.1 μm level for a board constituting an inspected object, on which a repeated pattern and a nonrepeated pattern are mixed, at high speed and with high accuracy, and it provides an apparatus to perform the method for resolving the above-described problems.

Further, the invention provides a method of inspecting a product for a particle or other defect with high sensitivity, even in a region having a high pattern density, and it provides an apparatus to perform the method.

Further, the invention provides a method of inspecting a product for a particle causing shortcircuiting of wirings, such as a defect or a particle having the shape of a thin film, with a high sensitivity, and it provides an apparatus to perform the method.

That is, according to the present invention, there is provided an apparatus for inspecting a board to detect a defect, comprising an illuminating light source; illuminating optical system means having a plurality of irradiating portions for irradiating an illuminating light flux emitted from the illuminating light source to a surface of the board from a plurality of directions that are different from each other, and an optical path switching portion for switching the illuminating optical flux among the plurality of illuminating portions; detecting optical system means having a variable magnification, including an object lens for condensing reflected diffracted light from the board illuminated by the illuminating optical system means; a focusing optical system having a variable magnification capable of focusing an optical image produced by the reflected diffracted light that has been condensed by the object lens by a desired focusing magnification and an optical detector for detecting an optical image focused by the focusing optical system to convert it to an image signal; A/D converting means for converting the image signal provided from the optical detector of the detecting optical system means into a digital image signal; and image signal processing means for processing the digital image signal that has been converted by the A/D converting means to detect a defect.

Further, according to the invention, a method of inspecting a board constituting an inspected object for detecting a defect, comprises the steps of irradiating an illuminating light flux emitted from an illuminating light source to a surface of the board, by continuously moved in one direction, from a skewed direction; detecting an optical image produced by reflected diffracted light generated from the board by use of a sensor; and processing an image signal detected by the sensor to inspect the defect; wherein an optical path of the illuminating light flux emitted from the illuminating light source is switched in accordance with the kind of particle defect to irradiate a surface of the board constituting the inspected object from different directions, and the enlarging magnification of the optical image produced by the reflected diffracted light from the board is changed in accordance with the density of a pattern formed at a region on the board constituting the inspected object, to thereby detect the defect using the sensor.

According to the invention, it is possible to achieve an effect of reducing the diffracted light from a circuit pattern on a board of an LSI pattern or the like and of detecting a small particle or defect of the 0.1 μm level, a particle or a defect shortcircuiting wirings, or a particle having the shape of a thin film at high speed and with high accuracy for a board constituting an inspected object that has a transparent film in the form of an oxide film or the like formed at a surface thereof and on which a repeated pattern and a nonrepeated pattern are mixed.

These and other objects, features and advantages of the invention will be apparent from the following more particular description of preferred embodiments of the invention, as illustrated in the accompanying drawings.

DESCRIPTION OF THE PREFERRED EMBODIMENTS

An explanation will be given of an embodiment according to the present invention with reference to the drawings.

A defect inspecting apparatus according to the invention makes it possible to inspect a product for a defect, such as a particle on a detected board of a wafer or the like, and for various defects which constitute a pattern defect, a micro scratch and the like, in various kinds of product and various fabricating steps, with high sensitivity and at high speed, particularly to detect a defect on a surface of a thin film formed on a surface of a wafer by separating the defect from a defect in the thin film. For that purpose, in a defect inspecting apparatus according to the invention, as shown in FIG. 1, an angle α of irradiating and a direction φ of irradiating a slit-like beam 201, which is illuminated by an illuminating optical system 10, are made to be variable in accordance with the object being inspected, a detecting optical system 20 is installed to constitute an imaging relationship with respect to the surface of the inspected object and a light receiving face of a detector 26, and the size of a detected pixel is set in accordance with the size of a detected defect by making the multiplication of the detecting optical system 20 variable, to thereby carry out an inspection.

Further, the defect inspecting apparatus according to the invention is also provided with a function of classifying the kind of defect by constituting a characteristic amount by a difference of the scattered light provided from a defect by, for example, illuminating light having a different irradiating angle.

First, a specific explanation will be given of a mode of carrying out the defect inspecting method according to the embodiment. Further, although in the following mode of carrying out the invention, an explanation will be given of a case of inspecting a small/large particle or micro scratch on a transparent film formed on a semiconductor wafer and a defect of a particle or a pattern defect in the transparent film, the invention is not limited to a semiconductor wafer, but is applicable also to a thin film board, a photomask, a TFT, a PDP or the like.

Figure 1:
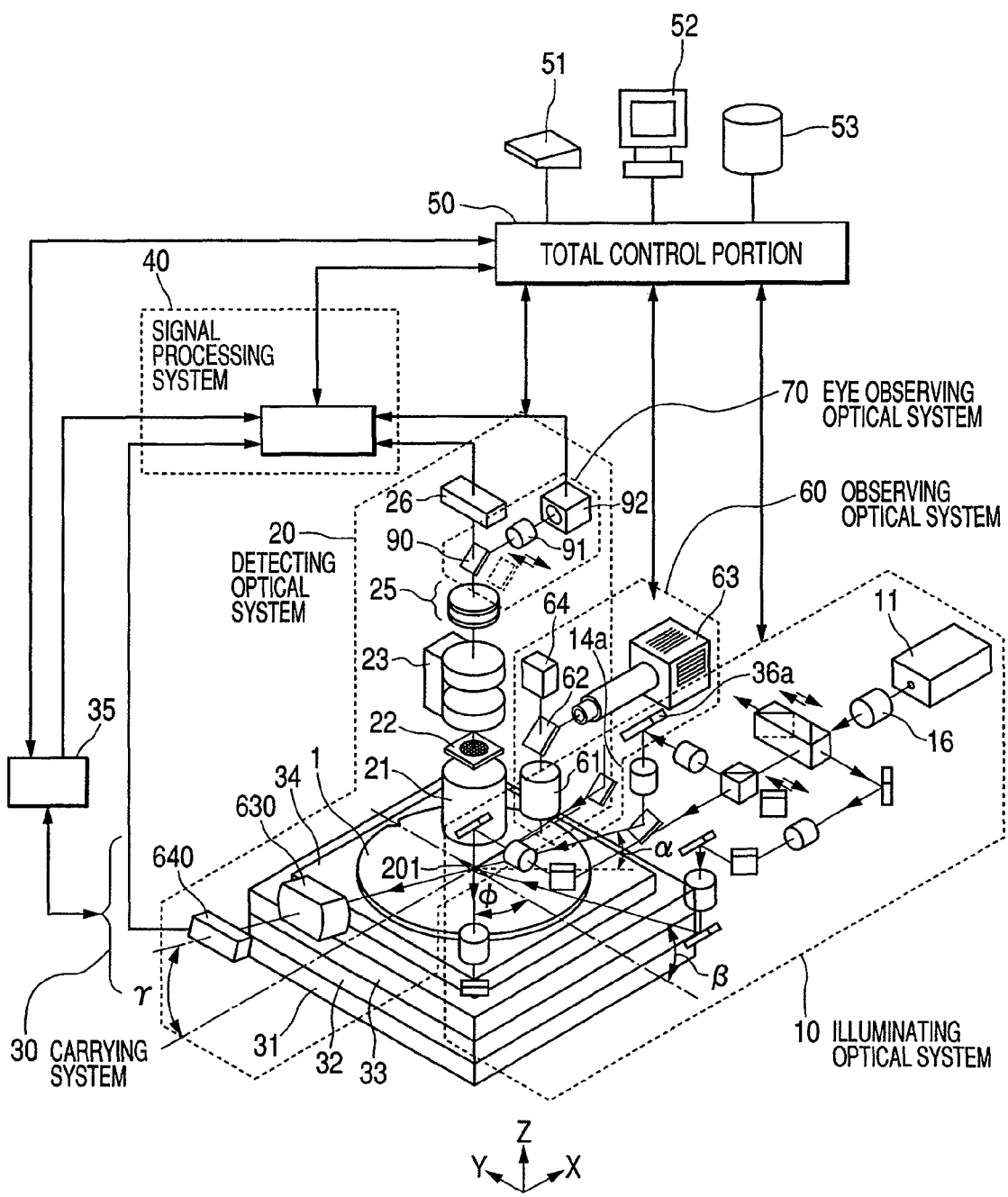
FIG. 1 is a prospective view showing an embodiment of a particle inspecting apparatus according to the invention.

As shown FIG. 1, the defect inspecting apparatus according to this embodiment is provided with a wafer carrying system 30 constituted by XYZ stages 31, 32, 33 arranged for movement within a conventional Cartesian coordinate system for mounting and moving a board 1 constituting an inspected object in the form of a wafer or the like provided from various product kinds or various fabricating steps and a controller 35; an illuminating optical system 10 for illuminating light emitted from a laser light source 11 onto the board 1 from a plurality of skewed directions after enlarging the light to a certain size by using a beam enlarging optical system 16, via a lens, a mirror and the like, the detecting optical system 20 having a variable multiplication constituted by an object lens 21, a spatial filter 22, a focusing lens 23, an optical filter group 420 and an optical detector 26 of a TDI image sensor or the like for detecting reflected diffracted light (or scattered light) from a region illuminated by the illuminating optical system 10; a signal processing system 40 for detecting a particle based on an image signal detected by the optical detector 26; an observing optical system 60 illuminating a surface of the wafer 1 by means of an illuminating light source 63, having a lens 61 and image taking means 64 for confirming the presence or absence, and a shape of a particle detected by inspection; and a total control portion 50 for setting inspection conditions or the like and controlling a total of the illuminating optical system 10, the inspecting optical system 20 having the variable multiplication, the carrying system 30 and the signal processing system 40. The total control portion 50 is provided with inputting/outputting means 51 (including also a keyboard or a network), displaying means 52 and a storing portion 53.

Further, the particle inspecting apparatus is provided with an automatic focusing control system (not illustrated) such that an image on the surface of the wafer 1 is focused on a light receiving face of the optical detector 26.

Figure 2A:
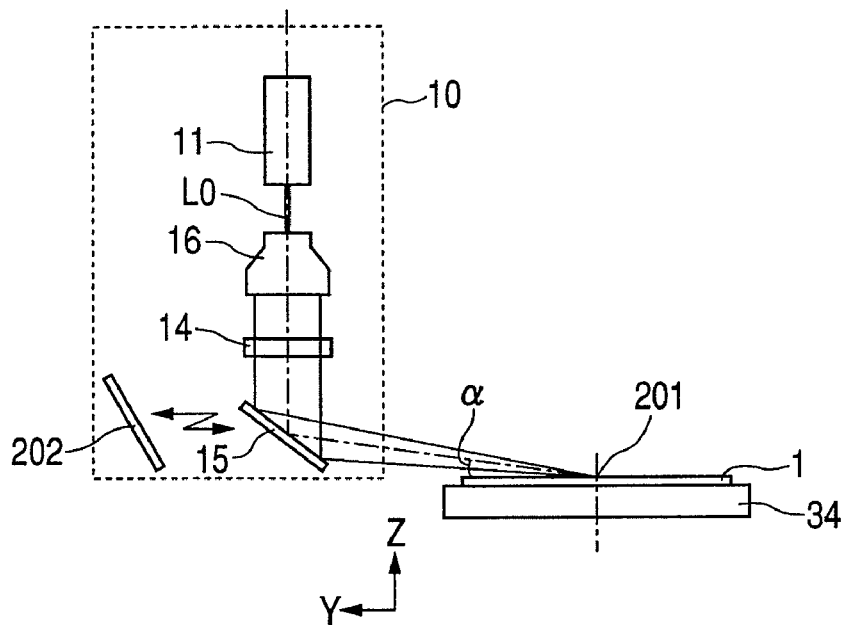
FIG. 2A is a diagram showing a side view and FIG. 2B is a diagrammatic prospective view of the illuminating optical system shown in FIG. 1.
Figure 2B:
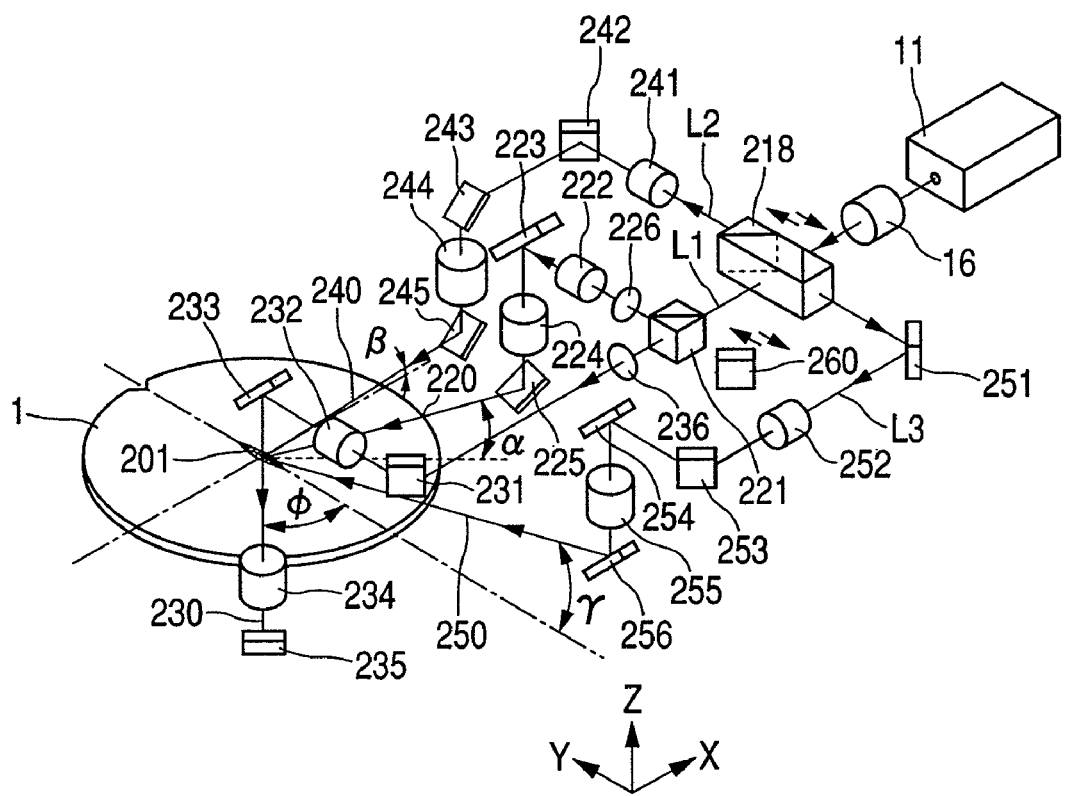

The inspecting apparatus has a constitution that is capable of illuminating a surface of the board 1 constituting the inspected object from a plurality of directions. As described in Patent publication 5, as shown in FIG. 2A, the illuminating optical system 10 is constituted by a beam enlarging optical system 16 constituted by, for example, a concave lens and a convex lens, not illustrated, for enlarging the light L0 emitted from the laser light source 11, a lens 14, a mirror 15 and the like. As shown in FIG. 2B, the inspecting apparatus of the present embodiment has a constitution capable of irradiating the slit-like beam 201 to the wafer (board constituting inspected object) 1 installed on the specimen installing base 34 planarly in a plurality of directions (four directions 220, 230, 240, 250 in FIG. 2B) and by a plurality of illuminating angles.

Here, the illuminating light is constituted by the slit-like beam 201 for achieving high speed formation of particle inspection by summarizingly detecting scattered light from a particle or a defect generated by illumination by light receiving elements arranged in one row. That is, the optical system is constituted such that the slit-like beam 201 illuminated on the wafer 1 aligned with the chip 202 by being directed in a scanning direction of the X stage 31 and a scanning direction of the Y stage 32 is condensed in the X direction and becomes parallel light in the Y direction, and the optical axis is adjusted to be orthogonal to the scanning direction X of the X stage 31, in parallel with the scanning direction Y of the Y stage 32 and also in parallel with the direction of pixel alignment of the optical detector 26. The 5 constitution achieves an effect of being capable of being easily positioned between chips when an image signal compares between chips. The slit-like beam 201 can be formed by providing, for example, a cylindrical lens in an optical path.

In the case of the focusing optical system as shown, for example, in FIG. 4, when the width in the X direction of the slit-like beam 201 of the illuminating light is equal to or smaller than the width in a short axis direction of the light receiving elements aligned in one row relative to the face of the inspection object, the loss of illuminated light can be sufficiently reduced. For example, when the width in the short axis direction of the light receiving element is 200 μm, and the magnification of the focusing optical system is 10 times, the illuminating width may be equal to or smaller than 20 μm. By slenderly narrowing the illuminating light, the optical energy is concentrated to a local portion of the inspection object to an amount sufficient to damage the inspection object. Therefore, it is important not to narrow the illumination more than necessary. Hence, in order to avoid damage to the inspection object, while preventing a loss of the illuminating light, it is preferable to constitute the arrangement such that "illuminating width"="width in short axis direction of light receiving element"÷"magnification of focusing optical system".

Figure 3A:
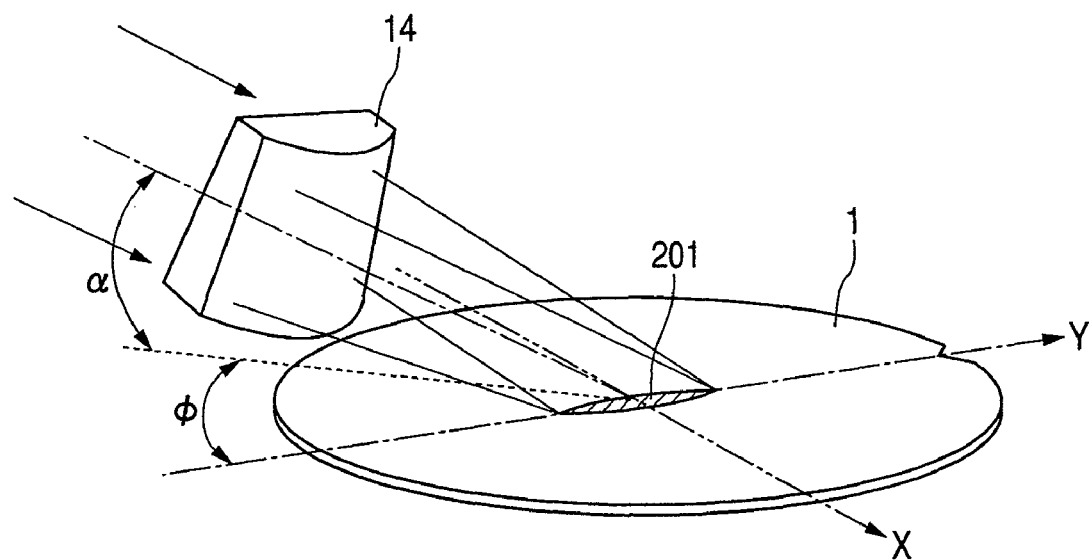
FIGS. 3A and 3B are diagrams illustrating a function of a conical curved face lens used in the illuminating optical system.
Figure 3B:
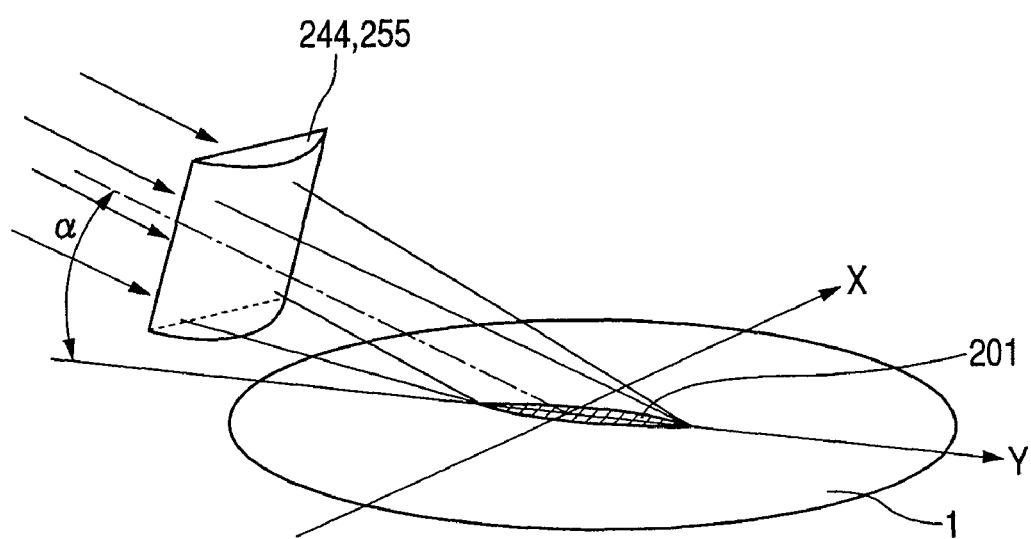

Here, in illuminating from the directions 220 and 230, it is necessary to form the slit-like beam 201 on the wafer 1 by irradiating laser light from a direction that is rotated in the Y axis direction of the wafer by an angle φ and is inclined in the X axis direction by an angle α. Therefore, the conical curved face lens 14 shown in FIG. 3A, in which the radius of curvature in a longitudinal direction is continuously being changed, is arranged in the optical path, and the slit-like beam 201 becomes parallel with the scanning direction of the Y stage. Further, in illuminating from the directions 240 and 250, the illumination comes from a direction which is the same as the direction of the scanning of the stage, and, therefore, the slit-like beam 201 can be formed by a cylindrical lens, as shown in FIG. 3B.

Further, there is a constitution which is capable of changing the illuminating angle α in accordance with the kind of a particle constituting an inspection object on the board 1 by switching the mirror 15 and a mirror 202, as shown in FIG. 2A, using a mechanism, based on the instruction received from the total control portion 50. There is a constitution in which, in any 15 case of the illuminating angle, the slit-like beam 201 includes an illuminating region for covering a direction 203 of alignment of the optical detector 26 and the slit-like beam 201 coincides with the wafer 1, even for illumination from any direction.

Thereby, illumination having parallel light in the Y direction and at a vicinity of φ=45 degrees can be realized. Particularly, by constituting the slit-like beam 201 of parallel light in the Y direction, diffracted light emitted from a circuit pattern, in which main groups of linear lines are directed in the X direction and the Y direction, is blocked by the spatial filter 22.

A method of fabricating the conical curved face lens 14 is described in Patent publication 5, and, therefore, an explanation thereof will be omitted.

The slit-like beam 201 is formed on the wafer 1 using a plurality of illuminating angles to deal with detection of particles of various types produced on the surface of the wafer 1. That is, there is constructed a constitution for detecting particles of an object by detection of a pattern defect or a particle having a low height on the board 1 constituting the detected object. The illuminating angle α is applied with an optical value that is empirically provided, since, when the angle is increased, the amount of reflected diffracted light from the circuit pattern is increased and the S/N ratio is lowered. As an example, when it is intended to detect a particle having a low height on the surface of a wafer, the illuminating angle α is preferably a small angle, for example, α is set to be 1 degree through about 5 degrees. Further, although the illuminating angle α may be increased when it is intended to detect a particle or a pattern defect between wirings in a wiring step, the illuminating angle may be set to be about 45 degrees through about 55 degrees, in view of the relationship of the S/N ratio of the pattern and the particle. Further, when there is a corresponding relationship between a step constituting an object of inspection and the kind of particle to be detected, the illuminating angle is set to be previously determined in an inspection recipe. In order to detect the above-described particle or pattern defect on the surface of wafer evenly, the illuminating angle may be set to a middle value of the above-described angles.

Further, with regard to a state of polarizing illumination, when, for example, the material of a surface of an inspecting object is a transparent material in the form of an oxide film or the like, P polarization illumination is provided with a transmittivity that is higher than that of S polarization illumination, with the result that it is easy to invade inside of the oxide film. Therefore, by changing the polarization of illumination, an inspection specified to a surface of the oxide film, or an inspection specified to a lower layer of the oxide film, can be carried out.

Further, in inspecting the oxide film, by setting a difference in the illuminating angle or the transmittivity by polarization, the scattering intensity of a defect differs by whether the defect is present on the surface of the oxide film, is in the oxide film or is a lower layer of the oxide film. A characteristic amount of the illuminating angle or the intensity of scattered light from the defect in illuminating the inspecting object when the polarization condition is changed, can be effective in classifying whether the defect is present on the surface of the oxide film.

Further, with regard to the illuminating direction φ, for example, in the case of a wiring step, by aligning a wiring pattern formed on the wafer and the illuminating direction, a particle between the wirings becomes easy to detect. Further, when the circuit pattern of the wafer is not a wiring pattern, but is a contact hole, a capacitor or the like, there is no specific directionality, and, therefore, it is preferable to illuminate the chip from a direction in the vicinity of 45 degrees. Further, in changing the illuminating angle, the illuminating angle may be changed by switching two mirrors having different angles, as shown in FIG. 2A, or the angle of a single mirror may be changed using rotating means, not illustrated.

Next, a method of changing the illuminating direction will be explained. A branching optical element 218, as shown in FIG. 2B, is constituted by a mirror, a prism or the like for transmitting or reflecting laser light L0 emitted from the laser light source 11 to guide it in three directions by moving the position thereof in the Y direction. Laser light L1 transmitted through the branch optical element 218 is branched to from transmitted light and reflected light by a half prism 221, for example, and the transmitted light is reflected by a mirror 235 again via a mirror 231, a beam diameter correcting optical system 232, a mirror 233, and a conical curved face lens 234 to form the slit-like beam 201 on the wafer 1 from the direction 230.

Meanwhile, the reflected light at the half prism 221 forms the slit-like beam 201 on the wafer 1 from the direction 220 by way of an optical path having the same function. Further, beam diameter correcting optical systems 222 and 232 adjust the beam diameter of the laser light incident on the conical curved face lens 14, such that the slit-like beam 201 irradiated to the wafer 1 is constituted to have the same size. Further, when a mirror 260 is installed in place of the half prism 235, the beam can be irradiated only from the direction 220 or the direction 230. Further, by inserting wavelength plates 226, 236 on the rear side of the half prism 235, the polarization direction of the irradiated laser beam also can be aligned.

Meanwhile, laser light L2 reflected by the branch optical element 218 transmits through the beam diameter correcting optical 241, thereafter, is reflected by mirrors 242 and 243, transmits through a cylindrical lens 244, is reflected by a mirror 245 again and forms the slit-like beam 201 on the wafer from the direction 240. Laser light L3 forms the slit-like beam 201 on the wafer 1 from the direction 250 by way of an optical path having the same function.

With regard to the illuminating directions 240 and 250, when a large number of wiring patterns formed on the wafer become parallel with the X direction in, for example, a wiring step, the direction of illumination can be aligned, and an effect of facilitating the detection of a particle between wirings is achieved.

Further, as the laser light source 11, although a high power laser having a wavelength of 532 nm of a YAG second harmonic is used, it is not necessary that the wavelength is 532 nm, but the laser may be an ultraviolet, a far ultraviolet, or a vacuum ultraviolet optical laser, or the light source may be a light source in the form of an Ar laser, a nitrogen laser, a He—Cd laser, an excimer laser, or a semiconductor laser. Generally, by making the laser wavelength short, the resolution of a detected image is promoted, and, therefore, a highly sensitive inspection can be carried out. For example, when the NA of the object lens 21 is about 0.4 in a case of the wavelength of about 0.34 μm and the NA of the object lens 21 is about 0.2 in the case of a wavelength of 0.17 μm, the incidence of diffracted light to the object lens 21 is increased and the detecting sensitivity can be promoted. Further, with regard to the use of a semiconductor laser or the like, a small-sized and a low cost apparatus can be realized.

Further, depending on the kind of defect to be detected, the surface shape or the material of an inspecting object, there is a case of promoting the contrast of a defect in a specific wavelength range of illumination. Hence, when a preference is given to a number of kinds of defects, a usable constitution may be obtained by selecting or mixing a plurality of illumination wavelengths.

Further, as a system for oscillating the laser, there is a continuous oscillation system or a pulse oscillation system. In the case of a pulse oscillation system, the output is dispersed for each pulse, and, therefore, it is preferable to be able to irradiate from 10 pulses to about several tens of pulses or more in acquiring data of one pixel in the scanning direction in a detected image.

Figure 4A:
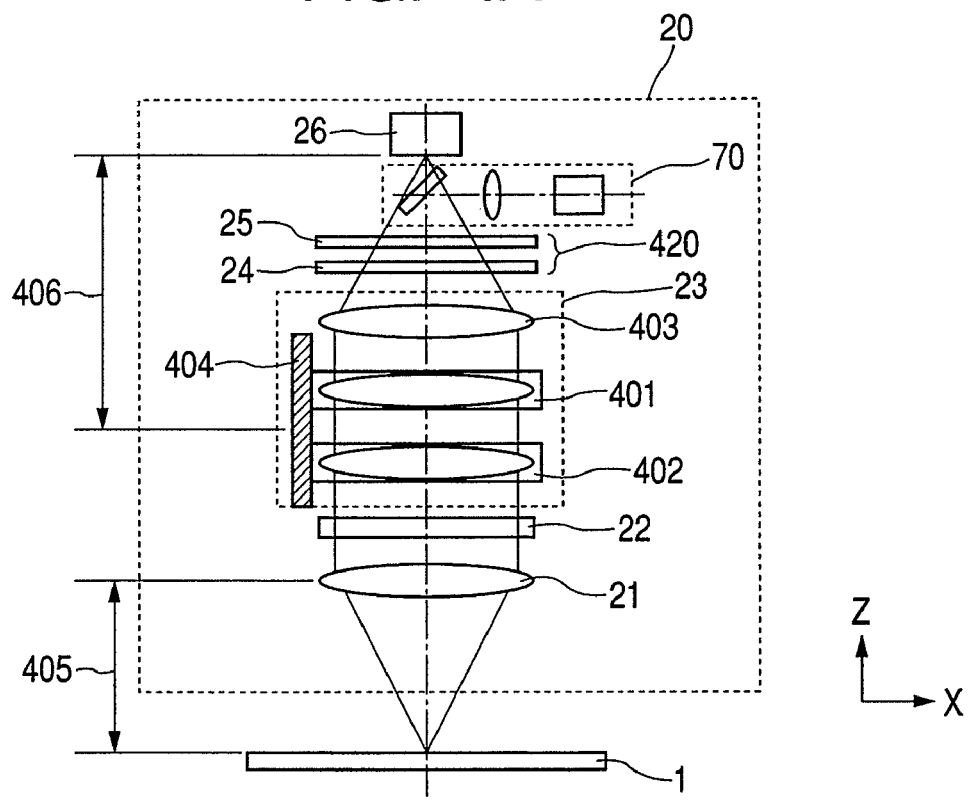
FIGS. 4A and 4B are diagrams illustrating the operation of making a multiplication variable portion of the detecting optical system shown in FIG. 1 variable.

Next, an explanation will be given of the detecting optical system 20 shown in FIG. 4A. The detecting optical system 20 is constituted to detect light that is illuminated by the illuminating optical system 10 and then is reflected and diffracted from the board 1 constituting the detected object of a wafer or the like by the optical detector 26 of a TDI image sensor or the like via the object lens 21, the spatial filter 22, the focusing lens (variable magnification focusing optical system) 23, and an optical filter group 25 comprising a concentration filter, a polarizer, or the like.

Figure 5A:
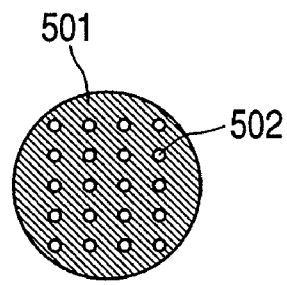
FIGS. 5A to 5C are diagrams illustrating the function of the eye observing optical system shown in FIG. 1.

The spatial filter 22 is provided with a function of blocking a Fourier transformed image by reflected diffracted light from a repeated pattern on the wafer 1 and transmitting scattered light from the particle, and it is arranged at a spatial frequency region of the reflecting lens 21, that is, a focusing position of Fourier transformation (in correspondence with the emitting eye). An eye observing optical system 70 comprises a mirror 90 installed in an optical path of the detecting optical system 20 and having a constitution capable of escaping in the X direction in inspection, a projecting lens 91, and a TV camera 92 for taking a reflected diffracted optical image 501 from a repeated pattern at the focusing position of Fourier transformation, as shown in FIG. 5A.

Figure 5B:
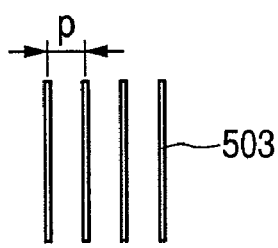
Figure 5C:
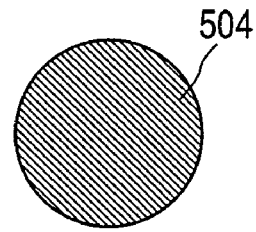

Here, as shown in FIG. 5B, the spatial filter 22 is provided with a constitution in which a plurality of light blocking portions 503 having a rectangular shape are aligned at variable intervals p, and it is provided at the focusing position of Fourier transformation and is constituted to change the interval p of the light blocking portion 503 by a mechanism, not illustrated, in accordance with the reflected diffracted optical image 501 from the repeated pattern at the focusing position of Fourier transformation taken by the TV camera 92. Thereby, as shown in FIG. 5C, when observed by the eye observing optical system 70, at the focusing position of Fourier transformation, the image can be adjusted to constitute an image 504 without a bright spot by the reflected diffracted optical image from the pattern. The operation can be executed based on the instruction of the total control portion 50 by processing a signal from the TV camera 92 using the signal processing system 40. Further, a light blocking pattern in accordance with the reflected diffracted optical image 501 may be formed based on the signal from the TV camera 92, not by the light blocking plate 503, but by using, for example, a liquid crystal board. Further, a plurality of light blocking patterns may be prepared and an optimum pattern may be selected for use based on the signal from the TV camera 92.

Further, the spatial filter 22 is also provided with a function of dealing with two or more repeated pitches in order to block diffracted light from patterns having different repeated pitches as in, for example, a memory cell portion and a direct peripheral circuit portion. For example, by arranging a second spatial filter that is shifted by several mm in the Z direction relative to the spatial filter in a linear shape, as shown in FIG. 5B, diffracted light of a plurality of patterns having different pitches can be blocked, and the number of regions capable of being inspected at a high sensitivity with a one time inspection can be increased. The second spatial filter may be disposed in parallel with the first spatial filter or it may be orthogonal thereto.

The inspecting apparatus is provided with a function of executing an inspection to detect the presence of a particle at high speed and with the function of executing an inspection at low speed, while maintaining a high sensitivity. That is, in the case of a detected object or detecting region in which the circuit pattern is fabricated with a high density, by increasing the magnification of the detecting optical system, although the inspecting speed is retarded, an image signal with a high resolution can be provided, and, therefore, a highly sensitive inspection can be executed. Further, in the case of a detected object or an inspecting region in which the circuit pattern is fabricated with a low density, by reducing the magnification, high speed inspection can be realized while maintaining a high sensitivity. Thereby, the size of a particle to be detected and the size of the detecting pixel can be optimized, and it is also possible to efficiently detect only scattered light from a particle by excluding noise from other than a particle.

Figure 4B:
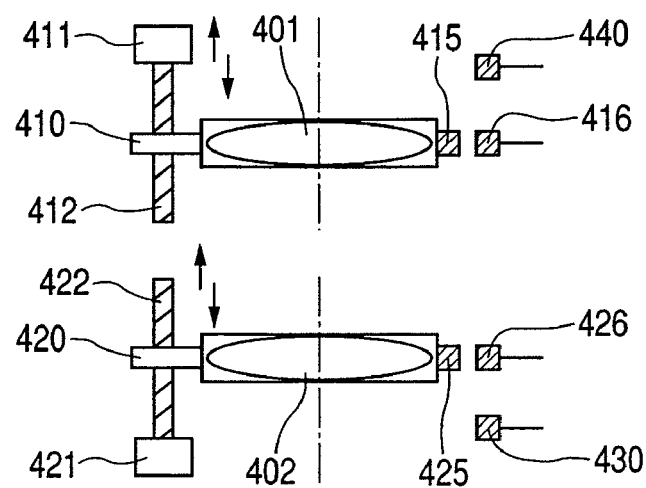

An explanation will be given of the operation of making the magnification of the detecting optical system variable with reference to FIG. 4B. The magnification of the detecting optical system is changed based on an instruction received from the total control portion 50. The focusing lens 23 is constituted by movable lenses 401, 402, a fixed lens 403 and a moving mechanism 404 to achieve a characteristic in which it is possible to make the magnification of a surface of a wafer focused on the detector variable without changing the positions of the object lens 21 and the spatial filter 22 in the Z direction in changing the magnification. That is, it is not necessary to change the relative positions of the board 1 constituting the detected object and the optical detector 26 even when changing the magnification, and the magnification can be changed by a simple constitution of the drive mechanism 404. Further, the size of a Fourier transformation face is not changed, and, therefore, an advantage is attained in that the spatial filter 22 need not be changed.

The magnification M of the detecting optical system 20 is characterized by the following Equation (1) in which the focal length 405 of the object lens 21 is designated by notation $f_1$ and the focal length 406 of the focusing lens 23 is designated by notation $f_2$.

$$M = f_1/f_2 \quad (1)$$

Therefore, in order to set the variable magnification of the detecting optical system 20 to the magnification M, since $f_1$ is a fixed value, the system is moved to a position in which $f_2$ becomes $(f_1/M)$. That is, in the inspecting apparatus, the magnification of the detecting optical system 20, which is arranged upward from a position where the wafer 1 is installed, is made to be variable by a simple constitution.

Next, the details of the moving mechanism 404 will be explained with reference to FIG. 4B. FIG. 4B shows the constitution used for moving the movable lenses 401 and 402 to specific locations. The movable lens 401 is held by a lens holding portion 410 and the movable lens 402 is held by a lens holding portion 420. The lens holding portion 410 and the lens holding portion 420 are moved to predetermined positions in the Z direction independently from each other by rotating a ball screw 412 using a motor 411 and by rotating a ball screw 422 using a motor 421.

A movable portion 415 or 425 of a positioning sensor is provided at a front end of the lens holding portion 410 or 420, which serves to hold the movable lens 401 or 402. The detecting portion 416 or 426 of the positioning sensor is provided at a position where the movable lens 401 or 402 is to be stopped. The lens holding portion is moved in the Z direction by driving the motor 411 or 421, and the positioning sensor 416 or 426, provided installing at a position of a desired magnification, detects the positioning sensor movable portion 415 or 425 to position the lenses. Further, a positioning sensor 440 serves to a limit sensor establishing an upper limit in the Z direction, and a positioning sensor 430 serves to a limit sensor establishing a lower limit in the Z direction. Here, an optical or a magnetic sensor is conceivable for use as the positioning sensor.

The operation is executed based on an instruction received from the total control portion 50, and the magnification is set in accordance with the pattern density of the board 1 constituting the inspected object which is mounted on a stage. For example, when a circuit pattern is formed with a high density, an inspection mode having a high sensitivity is constituted by selecting a high magnification; and, when the circuit pattern is formed with a low density, or when high speed inspection is needed, a low magnification is selected.

Further, it is also conceivable to unitize the movable lens portion and replace the magnification variable means with such a unit when the magnification is not changed frequently. In this case, there is an advantage of easily executing adjustment and maintenance.

Meanwhile, as described above, the illuminating angle is determined by the type of particle to be detected on an inspected object, and the illuminating angle and the illuminating direction of the illuminating optical system 10 are changed, in accordance with the board 1 constituting the inspected object mounted on a stage, based on an instruction received from the total control portion 50.

Meanwhile, in inspecting a product for a particle, it is necessary to also have the ability to inspect a multilayer wafer, the use of which has tended to increase in recent years due to high integration of semiconductor devices. A transparent film (for example, oxide film) is formed on a surface of the wafer in a step of forming multilayers, and a multilayer wafer is produced by repeating a step of forming a pattern thereon. There is an enhanced need for detecting only a particle on a surface of an oxide film in inspecting a wafer formed with an oxide film. Although, basically, it is possible to restrain the influence of reflected light from a matrix of pattern diffracted light or the like by reducing the illuminating angle α, there is a problem in that, by reducing the illuminating angle α, scattered light emitted from a particle on a side of regular reflection of illuminated light, that is, front scattered light, is increased, the incidence of scattered light on the detecting optical system provided above becomes small and the particle cannot be detected stably.

Figure 6:
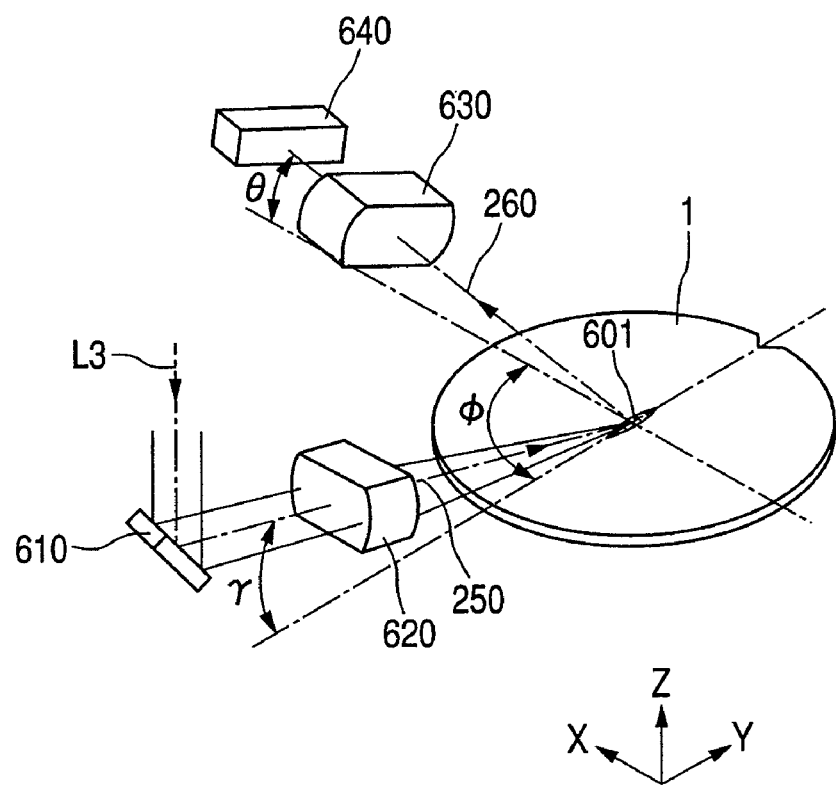
FIG. 6 is a diagram showing an embodiment of a first detecting optical system according to the invention.

Hence, according to the embodiment, as shown in FIG. 6, laser light L3, the beam diameter of which is enlarged is illuminated onto the wafer 1 by an illuminating angle γ relative to the surface of the wafer via a mirror 610 and a condensing lens 620 to thereby form slit-like beam 601. A detecting optical system comprising a focusing lens 630 and a detector 640 is arranged in a direction 260, which substantially orthogonally intersects with the illuminating direction 250, and in a direction of a horizontal angle φ and a detecting angle θ, to thereby detect side scattered light from a particle present on the surface of the thin film that has been emitted by the slit-like beam 601 illuminated onto the thin film formed on the surface of the wafer. The light receiving face of the detector 640 is arranged at a position representing an imaging relationship with the slit-like beam 601 via the focusing lens 630, and the focusing lens 630 is set with a focusing magnification such that the light receiving face of the detector faces the total illuminating range of the slit-like beam 601. By causing the detecting system to have this imaging relationship, the influence of stray light from other than the detecting object can be prevented, further, parallel processing can be executed by outputting signals in parallel from a plurality of pixels constituting the sensor, and, therefore, there is the advantage of achieving a high speed formation of inspection. In the inspection, the light receiving face of the detector is controlled such that the total illuminating range of the slit-like beam 601 is caught by an automatic focusing control system, not illustrated, such that the surface of the wafer is disposed at a constant position in the Z direction. Here, as the detector, a TDI sensor or a one-dimensional or two-dimensional image sensor is used. Further, it is also possible to block reflected diffracted light from a pattern by installing a spatial filter in the light path.

As the illuminating direction, the detected object may be illuminated from the direction 220 or the direction 230. However, when the detecting optical system comprising the focusing lens 630 and the detector 640 is arranged in the direction 260, the system is constituted to illuminate from the direction 220. In illumination from the direction 230, the detecting optical system comprising the focusing lens 630 and the detector 640 is arranged at a position on a side opposed to the focusing lens 630 and the detector 640 by constituting an axis of symmetry on the Y axis, also it is necessary to arrange the system at a position which does not interfere with the illuminating system arranged in the direction 230. Further, when detection is effected at a position on the side opposed to the focusing lens 630 and the detector 640 by interposing the Y axis by illuminating from the direction 230, it is preferable to set the detecting angle θ such that illuminating light from the direction 230 does not reach the detector 640. Thereby, a particle on the wafer can be accurately detected only by restraining the influence of reflected light from a matrix, such as pattern diffracted light or the like.

Figure 7A:
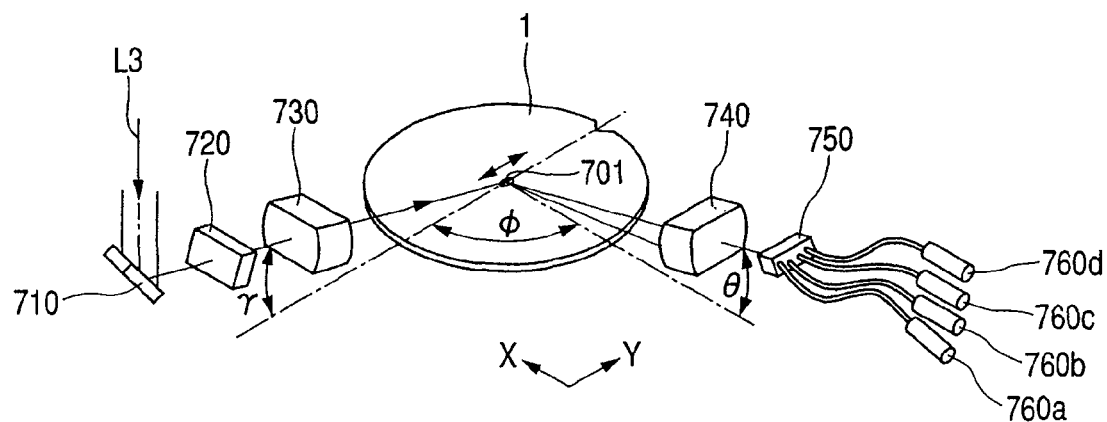
FIGS. 7A and 7B are diagrams showing another embodiment of a detecting optical system.
Figure 7B:
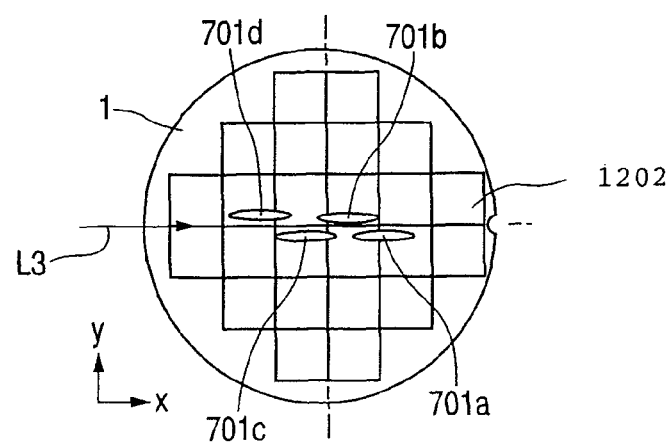
Figure 8A:
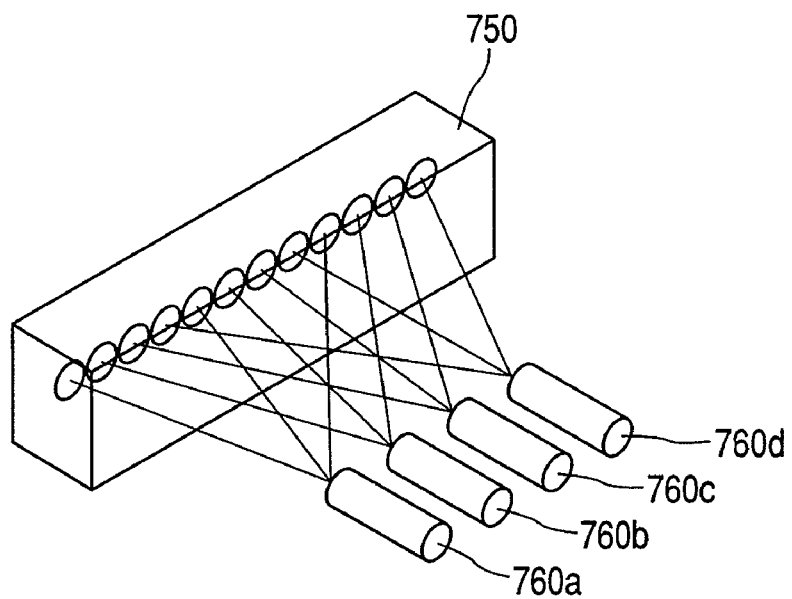
FIG. 8A is a diagram which illustrates an illumination portion and FIG. 8B is a diagram showing a detecting portion of the detecting optical system shown in FIG. 7.

Further, as shown in FIG. 7A, for example, laser light L3 may be illuminated by being scanned at high speed in the Y direction by deflecting means 730, and scattered light from a particle may be guided by distributing means 750, in the form of an optical fiber or the like, and detected by photoelectric conversion elements 760a through 760d, in the form of photomultipliers or the like. In this case, high speed formation of inspection is achieved by forming a group of a plurality of scanning spots on a wafer, as shown in FIG. 7B. Further, in detecting scattered light from a particle emitted from respective scanning spots 701a through 701d, as shown in FIG. 8A, the deviation of detection can be reduced by providing a constitution capable of picking up light information guided by the distributing means 750 at constant aligning intervals to be detected by the photomultipliers.

Figure 8B:
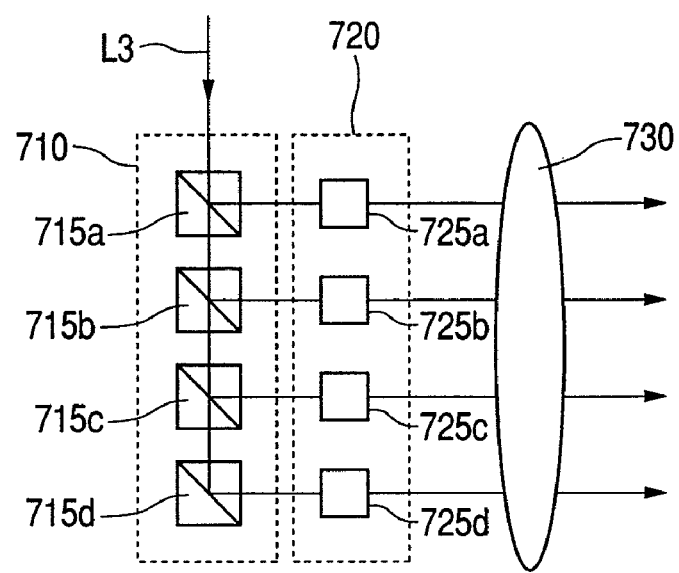
Figure 9:
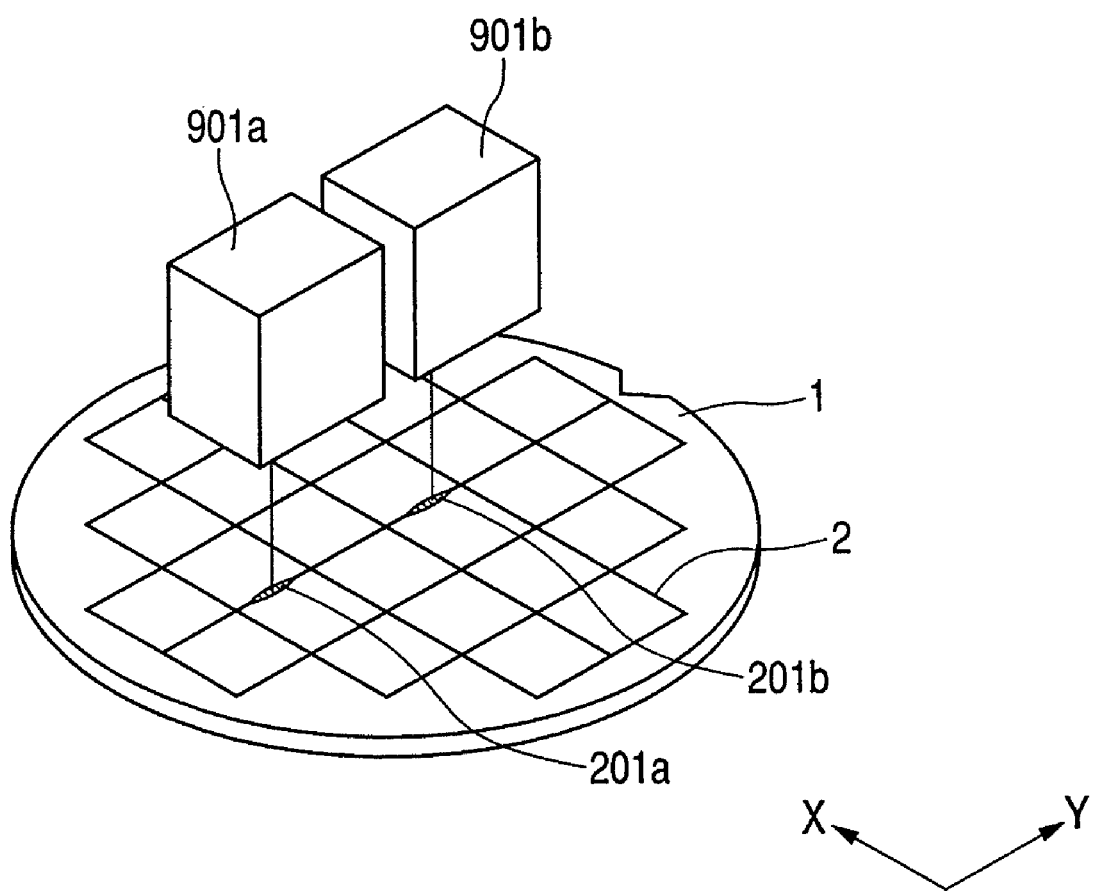
FIG. 9 is a diagram showing another embodiment of an inspecting apparatus.

Further, as shown in FIG. 8B, the plurality of scanning spots are constituted by dividing laser light L3 into a plurality of beams using branching means 710 and the respective spots are scanned in Y direction at the wafer by deflecting means 720. In this case, respective polarizers 725a through 725d modulate the respective light beams using frequencies that are different from each other. The respective photomultipliers 760a through 760d receive scattered light by scanning the respective spots and detecting scattered light from a particle emitted by scanning a specific spot by using a circuit, not illustrated, detecting electric signals outputted from the respective photomultipliers. Further, inspection can be constituted by high speed formation also by installing a plurality of detecting heads unitized with a laser illuminating system and a detecting system in a direction of alignment of the chip 1202, as shown in FIG. 7B, preferably, in conformity with the pitch of the chip, as shown in FIG. 9, instead of scanning the plurality of laser spots.

An ND filter 24, arranged at the detecting optical system 20, is used for adjusting the amount of light detected by the optical detector 26, and, when reflected light having a high brightness is received by the optical detector 26, the optical detector 26 is brought into a saturated state and cannot detect a particle stably. Although the ND filter 24 is not necessarily needed when the amount of illuminating light can be adjusted by the illuminating optical system portion 10, by using the ND filter 24, the width at which the amount of detected light is adjusted can be increased, and the light amount can be adjusted so as to be optimized for various inspected objects. For example, by combining the laser light source 11, so that the output is capable of being adjusted from 1 W through 100 W with ND filters in the form of a 100% transmission filter and a 1% transmission filter, the light amount can be adjusted from 10 mW to 100 W, and the light amount can be adjusted in a wide range.

The optical filter 25 is, for example, a polarizing element. The polarizing element is used for blocking a component of polarized light by reflected diffracted light emitted from an edge of a circuit pattern when illuminating polarized light by means of the illuminating optical system portion and transmitting a portion of the component of polarized light by reflected diffracted light emitted from the particle, and it is not necessarily needed according to the embodiment.

The optical detector 26 is an image sensor for receiving reflected diffracted light condensed by the condensing lens 23 so as to subject it to photoelectric conversion, and it may be provided in the form of a TV camera, a CCD linear sensor, a TDI sensor, an antiblooming TDI sensor or a photomultiplier.

Here, as a method of selecting the optical detector 26, in the case of an inexpensive inspecting apparatus, a TV camera or a CCD linear sensor is preferable; and, when weak light is detected with high sensitivity, for example, when a very small particle equal to or smaller than about 0.1 µm is to be detected, a sensor or a photomultiplier having a function of TDI (Time Delay Integration) is preferable.

The intensity of reflected diffracted light from a pattern differs according to the region of an inspecting object on a wafer. That is, at a memory cell portion formed with a repeated pattern and having a peripheral portion, the intensity of reflected diffracted light from other than a particle on the surface of the wafer is more intensified at the peripheral portion.

Figure 10A:
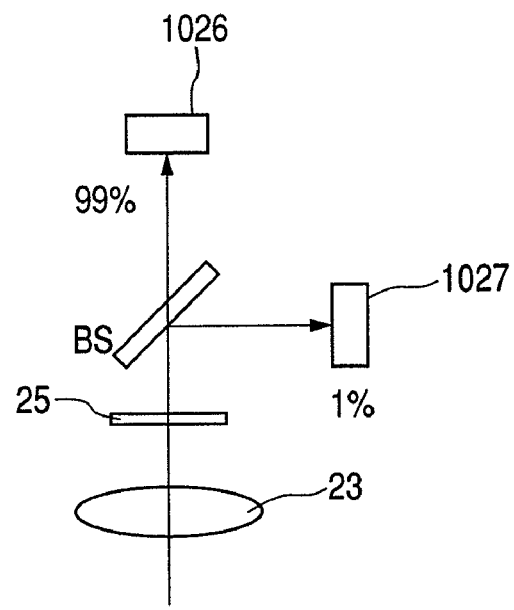
FIGS. 10A and 10B are diagrams illustrating another embodiment of an optical detector.
Figure 10B:
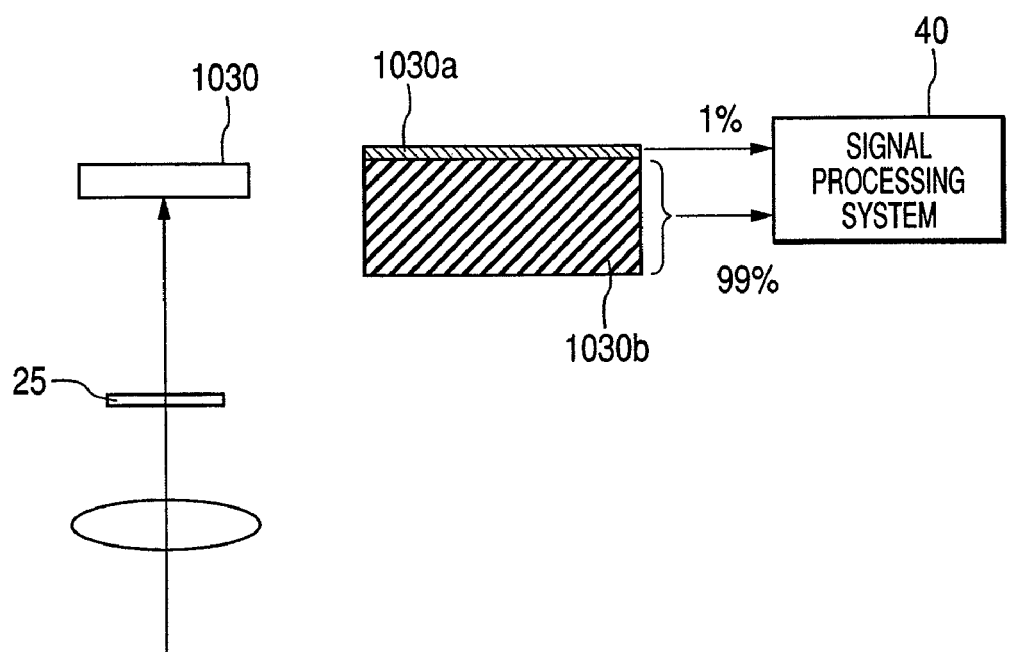

Therefore, when the dynamic range of light received by the optical detector 26 is large (when light for saturating a sensor is incident thereon), a sensor having an antiblooming function is preferable, and, as shown in FIG. 10A, a beam splitter having different transmittances and reflectances may be arranged at an optical path of the detecting optical system, and a detector may be installed at each optical path. In this case, even when strong light saturating one sensor 1026 is incident thereon, another sensor 1027 detects light having an attenuated light amount, and, therefore, a particle can be detected. Further, in the case of using a TDI sensor, as shown in FIG. 10B, it is also conceivable to use an element formed with a light receiving portion having a different number of stages for picking up a signal in an array of light receiving elements of, for example, 100 stages. For example, by dividing a portion of the pick up signal of 1 stage of an array of light receiving elements and a portion of the pick up signal from the remaining 99 stages, even in the case of incidence of strong light, and even when blooming is brought about at the portion where the signal of 99 stages is picked up, the blooming can be prevented at the portion where the signal of 1 stage of the array of light receiving elements is picked up, and respective output signals may be processed in the signal processing system 40.

Further, even when the diffracted light from the memory cell portion and a peripheral portion are simultaneously blocked by the spatial filter 20 in correspondence with a plurality of pattern pitches, the memory cell portion and the peripheral portion can be inspected with high sensitivity.

Figure 11A:
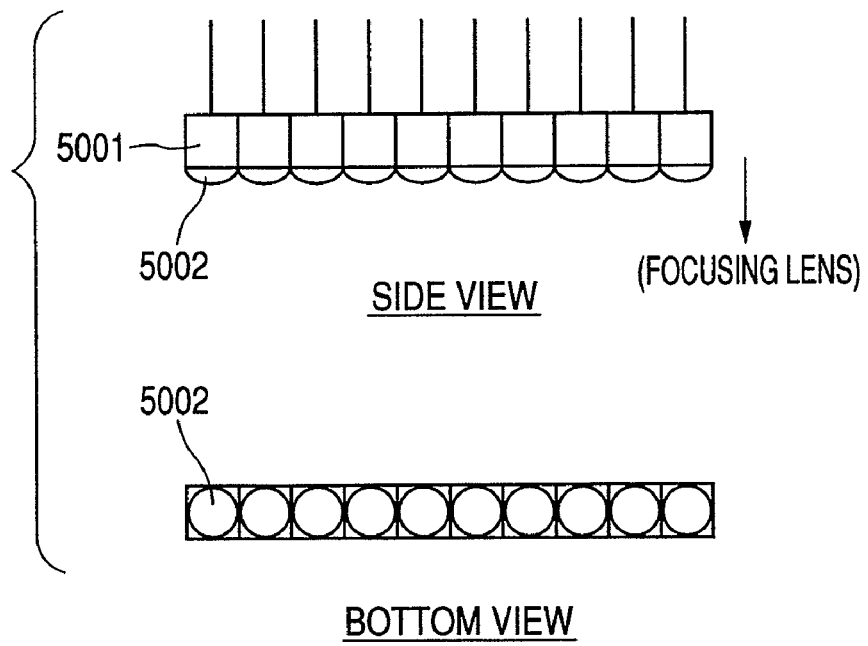
FIGS. 11A and 11B are diagrams illustrating another embodiment of an optical detector.
Figure 11B:
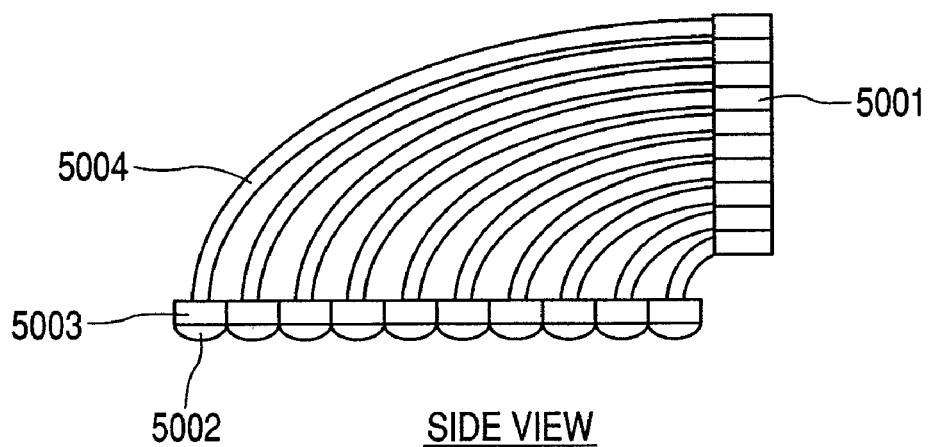

Further, when a photomultiplier is used, as shown in FIG. 11, a sensor aligned with the photomultipliers in a one-dimensional direction may be used. In this case, the sensor can be used as a highly sensitive one-dimensional sensor, and a highly sensitive inspection can be carried out. In this case, as shown in FIG. 11A, there may be a constitution for attaching a microlens 5002 to a side of the focusing lens 23 of a photomultiplier 5001 for detecting reflected diffracted light condensed by the focusing lens 23. Here, the microlens 5002 is provided with a function of condensing light, in a range equivalent to that of the face of the photomultiplier, to the photomultiplier 5001. Further, as shown in FIG. 11B, there may be a constitution for attaching an optical fiber 5004 via a jig 5003 installed downstream from the microlens 5002 and for attaching the photomultiplier 5001 at an output end of the optical fiber 5004. In this case, since the diameter of the optical fiber is smaller than the diameter of the photomultiplier, the sensor pitch can be made smaller than that of FIG. 11A, and, therefore, a sensor having a high resolution can be constituted.

Further, when a sensor aligned with a photomultiplier is used, in order to deal with the problem of aging deterioration of the sensor, a reference wafer for calibrating the sensitivity of an inspecting apparatus may be used. The inspecting apparatus can stably be operated by periodically inspecting the wafer for calibrating the sensitivity, thereby establishing a sensitivity for each photomultiplier based on a detecting signal at this occasion.

Next, the carrying system 30 will be explained. The stages 31, 32 are stages that are used for moving the specimen installing base 34 in the XY plane and are provided with strokes capable of moving a total face of the board 1 constituting the detected object to an illuminating area of the illuminating optical system 10. Further, the stage 33 is a Z stage and is provided with a function of moving the specimen installing base 34 in an optical axis direction (Z direction) of the detecting optical system 20. Further, the specimen installing base 34 is provided with a function of holding the wafer 1 by means of vacuum adsorption or the like and rotating the board 1 constituting the detected object in a plane. Further, the stage controller 35 is provided with a function of controlling the stages 31, 32, 33 and the specimen installing base 34.

Figure 12:
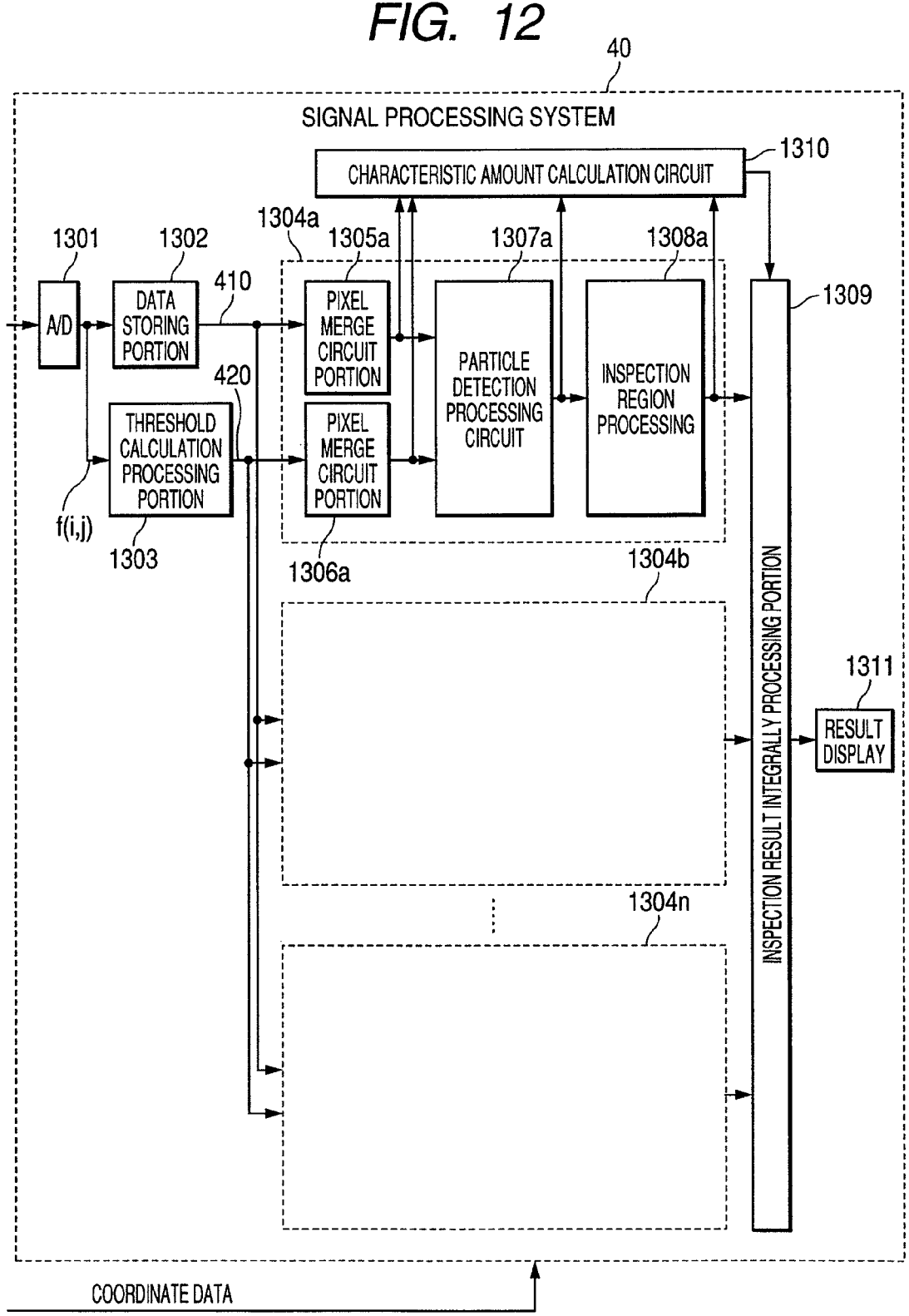
FIG. 12 is a block diagram showing the signal processing system shown in FIG. 1.
Figure 13:
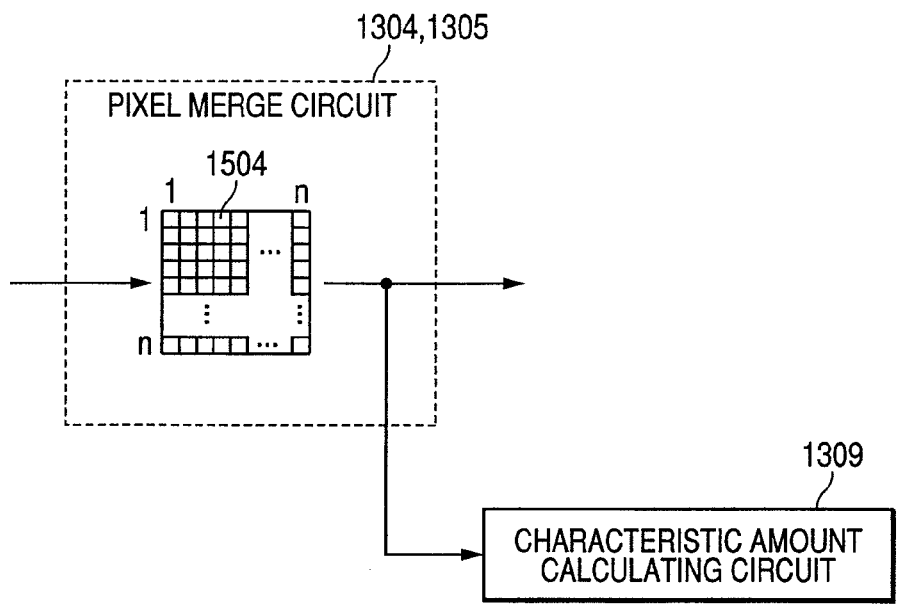
FIG. 13 is a diagram illustrating a threshold calculation processing portion.

Next, an explanation will be given of the signal processing system 40, which is used for processing an output signal from the optical detector 26 for receiving reflected diffracted light from the surface of the wafer 1 to subject it to photoelectric conversion, with reference to FIG. 12. The signal processing system 40 is constituted by an A/D converter 1301; a data storing portion 1302 for storing a detected image signal $f(i, j)$ that has been subjected to AND conversion; a threshold calculation processing portion 1303 for effecting a processing to calculate a threshold based on the detected image signal; particle detection processing portions 1304a through 1304n for effecting a processing to detect a particle for respective pixel images, based on a detected image signal 410 provided from the data storing portion 1302 and a threshold image signal (Th (H), Th (Hm), Th (Lm), Th (L)) 420 provided from the threshold calculation processing portion 1303; a characteristic amount calculating circuit 1310 for calculating a characteristic amount of scattered light provided by detecting a defect by low angle illumination, an amount of scattered light provided by detecting a defect by high angle illumination, a number of detected pixels showing a width of a defect or the like; an integral processing portion 1309 for classifying various defects of a small/large particle, a pattern defect, a micro scratch and the like on the semiconductor wafer; and a result display portion 1311. Respective ones of the particle detection processing portions 1304a through 1304n are constituted by pixel merge circuit portions 1305a through 1305n, 1306a through 1306n, particle detection processing circuits 1307a through 1307n, and inspection region processing portions 1308a through 1308n in correspondence with respective ones of merge operators of, for example, 1×1, 3×3, 5×5, ... n×n.

Particularly, the embodiment is characterized by the particle detection processing portions 1304a through 1304n, the characteristic amount calculating circuit 1310, and the integrally processing portion 1309.

Next, the operation of the signal processing system 40 will be explained. First, a signal provided by the optical detector 26 is digitized by the A/D converter 1301. The detected image signal $f(i, j)$ 410 is held in the data storing portion 1302 and is also transmitted to the threshold calculation processing portion 1303. A threshold image Th $(i, j)$ 420 is calculated for detecting a particle by the threshold calculation processing portion 1303, and a particle is detected by the particle detection processing circuit 1307 based on a signal processed by the pixel merge circuits 1305, 1306. The detected particle signal and the threshold image are subjected to a processing for a detected location by the inspection region processing portion 1308. Simultaneously, a characteristic amount (for example, an amount of scattered light provided by high angle illumination, an amount of scattered light provided by low angle illumination, a number of detected pixels of a defect or the like) is calculated by the characteristic amount calculating circuit 1309, based on signals provided from the pixel merge circuits 1305a through 1305n, 1306a through 1306n, the particle detection processing circuits 1307a through 1307n, and the inspection region processing portions 1308a through 1308n of the particle detection processing portions 1304a through 1304n provided for respective merge operators. The particle signal and the characteristic amount are integrated at the integral processing portion 1309, and an inspection result is displayed at the result display portion 1311.

Details thereof will be described as follows. First, the A/D converter 1301 is a circuit having a function of converting an analog signal provided by the optical detector 26 into a digital signal, and the conversion bit number is preferably from 8 bits to about 12 bits. This is because, when the bit number is small, the resolution of the signal processing becomes low, and it is difficult to detect a small amount of light, whereas, when the bit number is large, there is a disadvantage in that the A/D converter becomes expensive and the price of the apparatus becomes high. The data storing portion 1302 is a circuit for storing a digital signal that has been subjected to A/D conversion.

Next, the pixel merge circuit portions 1305, 1306 will be explained with reference to FIG. 10. The pixel merge circuit portions 1305a through 1305n, 1306a through 1306n are constituted by merge operators 1504 that are different from each other. The merge operator 1504 is a function of coupling respective ones of the detected image signal f (i, j) 410 provided from the data storing portion 1302 and the difference threshold image signal 420, comprising a detected threshold image Th (H), a detected threshold image Th (L), a detected threshold image Th (Hm) and a detected threshold image Th (Lm), provided from the threshold calculation processing portion 1303 in a range of n×n pixels, and it is, for example, a circuit for outputting an average value of n×n pixels. Here, the pixel merge circuit portions 1305a, 1306a are constituted by merge operators for merging, for example, 1×1 pixels, the pixel merge circuit portions 1305b, 1306b are constituted by merge operators for merging, for example, 3×3 pixels, the pixel merge circuit portions 1305c, 1306c are constituted by merge operators for merging, for example, 5×5 pixels, ... the pixel merge circuit portions 1305n, 1306n are constituted by merge operators for merging, for example, n×n pixels. The merge operator for merging 1×1 pixels outputs the input signals 410, 420 as they are.

Further, the influence of vibration of the stage or the like can be reduced by positioning images of image data used for forming the threshold, such as those of dies contiguous to each other, before executing the merge processing.

As described above, the threshold image signal comprises four image signals (Th (H), Th (Hm), Th (Lm), Th (L)), and, therefore, four merge operators Op are needed in each of the pixel merge circuit portions 1306a through 1306n. Therefore, detected image signals are outputted from the respective pixel merge circuit portions 1305a through 1305n as detected image signals 431a through 431n that are subjected to merge processing by the various merge operators 1504. On the other hand, the four threshold image signals (Th (H), Th (Hm), Th (Lm), Th (L)) are subjected to merge processing by the various merge operators Op1 through Opn and are outputted as the threshold image signals 441a (441a1 through 441a4) through 441n (441n1 through 441n4) from the respective pixel merge circuit portions 1306a through 1306n. Further, the merge operators in the respective pixel merge circuit portions 1306a through 1306n are the same.

The effect of merging a pixel will be explained here. According to the particle detecting apparatus of this embodiment, it is necessary to detect not only a small particle, but also a large particle in the shape of a thin film widened in a range of several μm without oversight. However, a detected image signal from the particle in the shape of a thin film is not necessarily enlarged, and, therefore, the SN ratio is low in a detected image signal by a unit of one pixel and oversight may be brought about. Hence, when the level of a detected image signal averaged by one pixel is designated by notation S, and an average dispersion is designated by σ/n, by cutting out the image by a unit of n×n pixels in correspondence with the size of the particle in the shape of a thin film to subject it to a convolution operation, the level of the detected image signal becomes $n^2 \times S$ and the dispersion (N) becomes $n \times \sigma$. Therefore, the SN ratio becomes $n \times S/\sigma$. On the other hand, when the particle in the shape of a thin film is going to be detected by the unit of one pixel, the level of the detected image signal becomes S, the dispersion becomes σ and, therefore, the SN ratio becomes S/σ. Therefore, the SN ratio can be increased by n times by cutting out the image by the unit of n×n pixels in correspondence with the size of a particle having the shape of a thin film to subject it to a convolution operation.

With regard to a small particle of about a unit of one pixel, the level of the detected image signal detected by the unit of one pixel becomes S, the dispersion becomes σ, and, therefore, the SN ratio becomes S/σ. When it is assumed that, the image is cut out by a unit of n×n pixels for a small particle of about the unit of one pixel to subject it to a convolution operation, the level of the detected image signal becomes $S/n^2$, the dispersion becomes $n \times \sigma$ and, therefore, the SN ratio becomes $S/n^3/\sigma$. Therefore, with regard to a small particle of about the unit of one pixel, the SN ratio can be increased by the signal of the unit of a pixel as it is.

Further, according to this embodiment, although an explanation has been given using an example in which the range of merging in a square shape (n×n pixels) has been employed, the range of merging may be constituted by a rectangular shape (n×m pixels). In this case, the range of merging of the rectangular shape is effective when a particle having a directionality is detected or, although a pixel detected by the optical detector 26 is rectangular, when the signal processing is intended to involve processing by a pixel in a square shape.

Further, although the function of the merge operator in this embodiment has been explained by reference to an example of outputting an average value of n×n pixels, a maximum value or a minimum value or a central value of n×n pixels may be outputted. When the central value is used, a stable signal is provided. Further, the average value of n×n pixels multiplied by or divided by a specific value may be constituted as an output value.

Next, the inspection region processing portions 1308a through 1308n will be explained. The inspection region processing portions 1308a through 1308n are used when the data of a region (including a region in the chip) which is not necessary for inspection is removed from a signal of a particle in the form of a defect provided by specifying the chip from the particle inspection processing circuits 1307a through 1307n, when the detection sensitivity is changed for respective regions (including a region in the chip), and when a region intended to be inspected is conversely selected. When, for example, the detection sensitivity may be low at a region on the board 1 constituting the inspected object, the inspection region processing portions 1308a through 1308n may set a threshold of the region provided from the threshold calculating portion 1411 of the threshold calculation processing portion 1303 to be high, or there may be constituted a method of leaving only data of a particle of a region to be inspected based on coordinates of the particle obtained from data of particles outputted from the particle detection processing circuits 1307a through 1307n.

Here, a region at which the detection sensitivity may be low is, for example, a region where the density of a circuit pattern is low in the board 1 constituting the detected object. An advantage of lowering the detection sensitivity resides in an efficient reduction in the number of pieces of detection. That is, in an inspecting apparatus having a high sensitivity, there is a case of detecting several tens of thousands of particles. In this case, what is truly important is a particle of a region at which a circuit pattern is present, and it is a shortcut to deal with the important particle for increasing the yield in fabricating a device. However, when the total region on the board 1 constituting the detected object is inspected using the same sensitivity, since an important particle and an unimportant particle are mixed, the important particle cannot be easily sampled. Hence, in the inspection region processing portions 1308a through 1308n, by lowering the detection sensitivity of a region on which a circuit pattern is not present and which does not significantly influence the yield based on CAD information or threshold map information in the chip, the important particle can be efficiently sampled. However, the method of sampling the particle is not limited to a changing of the detection sensitivity, but the important particle may be sampled by classifying the particles, as will be mentioned later, or the important particle may be sampled based on the size of the particle.

Next, the integral processing portion 1309 and the inspection result display portion 1311 will be explained. The integral processing portion 1309 is provided with a function of integrating a result of detecting a particle that is subjected to parallel processing by the image merge circuits 1305, 1306, integrating the characteristic amount calculated by the characteristic amount calculating circuit 1310 and the particle detecting result and transmitting the result to the result display portion 1311. It is preferable to execute the inspection result integral processing by use of a PC or the like to facilitate a change to the processing content.

First, the characteristic amount calculating circuit 1310 will be explained. The characteristic amount is a value representing a characteristic of a detected particle or defect, and the characteristic amount calculating circuit 1310 is a processing circuit for calculating the characteristic amount. As the characteristic amount, there are, for example, the amount of reflected diffracted light (amount of scattered light) (Dh, Dl) from a particle or a defect provided by high angle illumination and low angle illumination, the number of detected pixels, the shape and direction of an inertia main axis of a region for detecting a particle, the location of the detection of a particle on a wafer, the kind of circuit pattern of a matrix, and the threshold used in detecting a particle.

Figure 14:
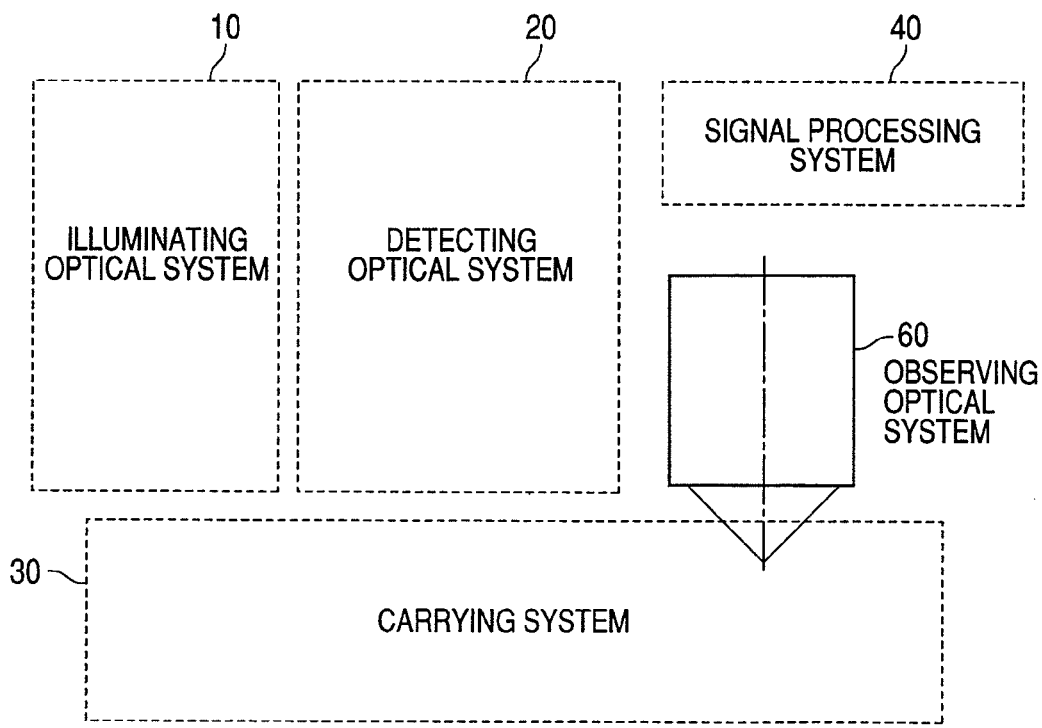
FIG. 14 is a block diagram showing an embodiment to which an observing optical system.

FIG. 14 shows an embodiment of a defect inspecting apparatus with an attached microscope. According to the embodiment, there is a constitution capable of confirming a particle detected by inspection by use of the observing optical system 60. The observing optical system 60 observes an image by moving a detected particle (including false information) on the wafer 1 to a position of a field of view of the microscope of the observing optical system 60 by moving the stages 31, 32.

An advantage of providing the observing optical system 60 resides in the fact that the detected particle can be observed at once without moving the wafer to a review apparatus of the SEM or the like. By observing the detected object at once by use of the inspecting apparatus, the cause of producing the particle can be specified swiftly.

Further, an image of the TV camera 64 of the observing optical system 60 is also provided with a function of displaying a detected particle on a color monitor commonly used by a personal computer. The system is capable of partially irradiating a laser, and executing inspection by scanning the stages centering on coordinates of the detected particle and marking an image of scattered light of the particle and the position of the particle to display this information on the monitor. Thereby, it can be confirmed whether a particle actually has been detected. Further, a partial image obtained by scanning the stages can acquire also an image for inspecting a die contiguous to a die at which the particle is detected, and, therefore, comparing and confirming can be executed at the location.

Further, the observing optical system 60 may be a microscope constituting a light source producing visible light (for example, white light) or a light source producing ultraviolet light. Particularly, in order to observe a small particle of the 0.1 μm level, a microscope having a high resolution, for example, a microscope using ultraviolet light, is preferable. Further, when a microscope employing visible light is used, there is an advantage of providing color information of a particle, thereby making it possible to easily recognize a particle.

Further, since transmittance differs according to the wavelength of the light source depending on the material of the surface of an inspecting object, there is a case in which it is difficult to confirm a defect using a light source in a wave length band different from the illuminating wavelength used in inspection. Therefore, there may be a constitution that is capable of selecting a light source in a band proximate to an inspecting wavelength.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

The invention claimed is:

1. A method of detecting a defect by inspecting a specimen including the steps of:
illuminating a surface of a specimen on which plural patterns are formed with an elongated shape light flux from a first elevation angle, said specimen being set on a stage which is continuously moving in one direction;
capturing an image of the specimen illuminated by the elongated shape light flux with a linear image sensor of an optical detecting unit installed in a second elevation angle direction; and
detecting a defect on the specimen by processing a signal output from the linear image sensor,
wherein in the step of illuminating, said elongated shape light flux is formed from a pulsed ultraviolet laser emitted from a pulsed ultraviolet laser source, said elongated shape light flux illuminates the specimen more than 10 pulses in acquiring data of one pixel in the continuously moving direction in the detected image, a longitudinal direction of said elongated shape light flux is perpendicular to a direction along which said stage is continuously moving, and said elongated shape light flux is shaped to have a width on said specimen in a direction perpendicular to a longitudinal direction of the elongated shape light flux corresponding to a magnification of the optical detecting unit and a size in a short axis direction of a light receiving elements array of linear image sensor, and
wherein the stage moves within a plane defined by two axes of a Cartesian coordinate system and the elongated shape light flux is directed along a third axis of the Cartesian coordinate system.

2. An apparatus for inspecting a defect on a specimen comprising:

an ultraviolet laser light source which emits a pulsed ultraviolet laser having an elongated shape;

a stage which continuously moves at least in one direction, and on which a specimen having plural patterns are formed thereon is mounted;

an illuminator which illuminates the specimen from a first elevation angle direction relative to the specimen with the pulsed ultraviolet laser having the elongated shape on said specimen;

an optical image detecting unit having a linear image sensor and installed in a second elevation angle direction relative to the specimen for detecting an image of the sample illuminated by the elongated shape pulsed ultraviolet laser; and an image signal processing means for processing an image signal output from the linear image sensor to detect defects on the specimen, wherein, said illuminator illuminates the specimen with the pulsed ultraviolet laser having the elongated shape more than 10 pulses in acquiring data of one pixel in the continuously moving direction in the detected image, a longitudinal direction of said elongated shape light flux on said specimen is perpendicular to a direction along which said stage is continuously moving, and said elongated shape light flux is shaped to have a width in a direction perpendicular to a longitudinal direction of the elongated shape light flux corresponding to a magnification of the optical image detecting unit and a size in a short axis direction of a light receiving elements array of said linear image sensor, and wherein the stage moves within a plane defined by two axes of a Cartesian coordinate system and the elongated shape light flux is directed along a third axis of the Cartesian coordinate system.

3. A method according to claim 1, wherein in the step of illuminating, said width of the elongated shape pulsed ultraviolet laser illuminated on said specimen in a direction perpendicular to a longitudinal direction of the elongated shape light flux is equal to or smaller than an amount calculated from dividing a width in the short axis direction of the light receiving elements array of said linear image sensor by a magnification of the optical image detecting unit.

4. A method according to claim 1, wherein in the step of illuminating, said elongated shape pulsed ultraviolet laser is a P polarized laser.

5. A method according to claim 1, wherein in the step of illuminating, said elongated shape pulsed ultraviolet laser is a S polarized laser.

6. A method according to claim 1, wherein in the step of illuminating, said first elevation angle is between 1 degree and 5 degrees.

7. A method according to claim 1, wherein in the step of capturing, said image of the specimen illuminated by the elongated shape light flux is captured by the image sensor through a polarizing element.

8. A method according to claim 1, wherein in the step of detecting, defects on said specimen are detected by processing the signal output from the linear image sensor in parallel.

9. An apparatus according to claim 2, wherein said illuminator, said width of the elongated shape pulsed ultraviolet laser illuminated on said specimen in a direction perpendicular to a longitudinal direction of the elongated shape ultraviolet laser is equal to or smaller than an amount calculated from dividing the width in the short axis direction of the light receiving elements array of said linear image sensor by a magnification of the optical image detecting unit.

10. An apparatus according to claim 2, wherein said illuminator illuminates said specimen with a P polarized laser having said elongated shape.

11. An apparatus according to claim 2, wherein said illuminator illuminates said specimen with a S polarized laser having said elongated shape.

12. An apparatus according to claim 2, wherein said first elevation angle of said illuminator is between 1 degree and 5 degrees.

13. An apparatus according to claim 2, wherein said optical image detecting unit further installs a polarizing element, and said image sensor captures said image of the specimen illuminated by the elongated shape light flux through the polarizing element.

14. An apparatus according to claim 2, wherein said image signal processing means processes the image signal output from the linear image sensor in parallel.

* * * * *